United States Patent [19]

Watanabe et al.

[11] Patent Number: 5,005,434
[45] Date of Patent: Apr. 9, 1991

[54] AUTOSAMPLER WITH A MEANS FOR DETECTING AIR BUBBLE IN SPECIMEN

[75] Inventors: Yoshio Watanabe, Hitachi; Mamoru Taki, Oomiya; Junkichi Miura; Masao Kamahori, both of Hitachi; Hiroyuki Miyagi, Kokubunji; Yasuhide Matsumura, Hachiouji; Masafumi Kanetomo, Tokyo, all of Japan

[73] Assignee: Hitachi, Ltd., Tokyo, Japan

[21] Appl. No.: 390,720

[22] Filed: Aug. 8, 1989

[30] Foreign Application Priority Data

Aug. 27, 1988 [JP] Japan ................ 63-213356

[51] Int. Cl.$^5$ ........................................ G01N 35/06
[52] U.S. Cl. ................................................ 73/864.21
[58] Field of Search ........... 73/864.01, 864.21–864.25, 73/864.86, 864.87, 865.8, 864.21; 422/70, 100; 356/36, 72, 433–437, 440

[56] References Cited

U.S. PATENT DOCUMENTS

| 3,699,348 | 10/1972 | Hocherl | 73/864.24 |
| 4,312,341 | 1/1982 | Zissimopoulos et al. | 356/440 |
| 4,318,884 | 3/1982 | Suzuki | 422/63 |
| 4,399,711 | 8/1983 | Klen | 422/100 |
| 4,419,903 | 12/1983 | Jackson | 73/864.01 |
| 4,829,837 | 5/1989 | Telfer | 73/863.01 |

FOREIGN PATENT DOCUMENTS

| 2133797 | 1/1973 | Fed. Rep. of Germany | 356/436 |
| 0163849 | 10/1982 | Japan | 356/436 |
| 0003034 | 1/1986 | Japan | 356/436 |

Primary Examiner—Robert Raevis
Attorney, Agent, or Firm—Antonelli, Terry, Stout & Kraus

[57] ABSTRACT

An autosampler consists of a needle to draw specimen from a specimen container into a passage therein; a block having a passage that follows the passge in the needle; a suction mechanism for drawing in the specimen by suction through the passages in the needle and the block; a discharge mechanism for discarding the specimen drawn in by the suction mechanism; and a detecting device for detecting air bubble in the specimen, the detecting device being embedded in the block in such a manner as to face the passage in the block. The detecting device detects the air bubbles in the specimen according to changes in physical or chemical properties of the specimen passing through the passage in the block. The discharge mechanism is activated by the detecting device to discharge air-mixed specimen. When even a small amount of air is drawn into the passage from the specimen container, in which only a small amount of specimen is contained, the air specimen can reliably be distinguished from normal specimen by this autosampler. Therefore the reliability of the system using the autosampler can be significantly improved.

8 Claims, 8 Drawing Sheets

AUTOSAMPLER WITH A MEANS FOR DETECTING AIR BUBBLE IN SPECIMEN

BACKGROUND OF THE INVENTION

This invention relates to an autosampler which detects air bubbles in specimen and, more particularly, to an autosampler used in liquid chromatograph or automatic chemical analyzer to check whether the liquid sample has been drawn from a sample container into the analyzing apparatus without bubbles, being mixed therein.

Conventional autosamplers known which detect by use of a sensor air bubbles mixed in the liquid specimen to be analyzed and then remove the air bubbles from the liquid specimen.

The Japanese Patent Laid-Open No. 167470/1987 describes a method of removing the air portion from the specimen by detecting the air portion in the liquid specimen drawn in through a needle from a specimen container and by removing the air bubble from the liquid specimen analyzing passage.

In this method, the specimen taken in from the needle is fed through a long passage to a 6-way valve, and at the inlet thereof the air bubbles are detected. Thus, the air bubbles cannot be detected without taking in a significant amount of specimen from the needle. And when the air portion in the liquid specimen is to be removed from the needle, a large amount of the liquid specimen has to be discarded along with the air bubble.

Furthermore, since the air portion in the liquid specimen is detected in a wide passage at the inlet of the 6-way valve, the fine air bubbles are very difficult to detected. While the detection may be made possible by narrowing the inlet, this will also increase the flow speed of specimen making it difficult to discharge the unwanted air-mixed specimen at an appropriate timing by changing the slow-response 6-way valve. Therefore, the above air detection method is not suitable for the autosampler that makes analysis and measurement of a very small amount of specimen which may easily trap fine bubbles.

The Japanese Patent Laid-Open No. 132064/1982 and 275659/1986 describe a method of detecting air bubbles by installing electrodes in a tube connected to a suction nozzle through which the liquid specimen is drawn in and by checking changes in electrostatic capacitance. This method, too, has a long passage from the specimen suction point to the air detecting point and therefore has similar drawbacks to those stated above.

Therefore, in these conventional techniques, it is difficult to detect fine bubbles that were mixed in a very small amount of specimen when the specimen was drawn in by suction. If the bubbles are detected, the conventional techniques have a problem of having to discharge a significant amount of the liquid specimen in order to remove the air portion such as air bubbles.

In the Japanese Patent Laid-Open No. 85355/1985, a method is disclosed for checking the specimen optically at a location near the nozzle. This method, however, is to check the concentration of a chemical substance in the specimen and is not used to detect the air bubbles contained in the specimen solution.

SUMMARY OF THE INVENTION

The object of this invention is to provide an autosampler which reliably detects an air portion such as fine air bubbles when a very small amount of liquid specimen is drawn in and which removes the air portion mixed in the specimen while keeping the wasted amount of the specimen to a minimum.

In analyzing or measuring a small amount of specimen, a very fine needle is often used to introduce by suction the specimen in a container into a measuring passage. If the air portion could be detected at the tip of the fine needle, it would be possible to remove the air portion from the specimen with a loss of a very small amount of the specimen by discharging the air portion in the specimen from that needle end. However, it is structurally difficult to mount such a detector at the tip of the fine needle. It may be possible, for example, to electrically insulate the needle normally made with metal and mount electrodes of the detector on it. The needle construction, however, necessarily becomes complex as it has to connect the electrodes to the detector thereon, and is thus not suitable for needles as expendable parts. To overcome these problems, this invention introduces a construction in which a block that rigidly supports a needle is provided with a fine passage following the fine needle passage and in which a detecting means is arranged in the block in such a manner as to face the passage in the block. With this construction, fine air portion such as bubbles pass immediately in front of the air detecting means and thus can reliably be detected. Moreover, the air portion in the specimen can be removed by discharging only a small amount of specimen from the needle tip, minimizing the wasted amount of specimen.

DETAILED DESCRIPTION OF THE PREFERRED EMBODIMENTS

Figure 1A:
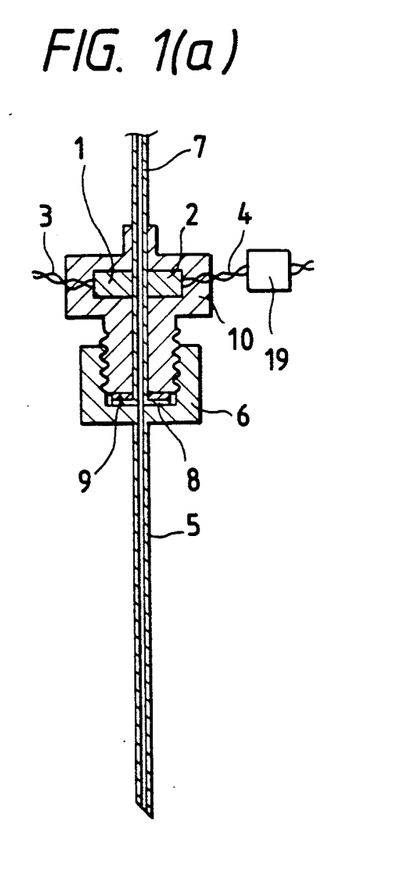
FIGS. 1a and 2a are respectively vertical cross-sectional views of embodiments of this invention in which a light source and a light receiving member are embedded in the block supporting the needle.
Figure 1B:
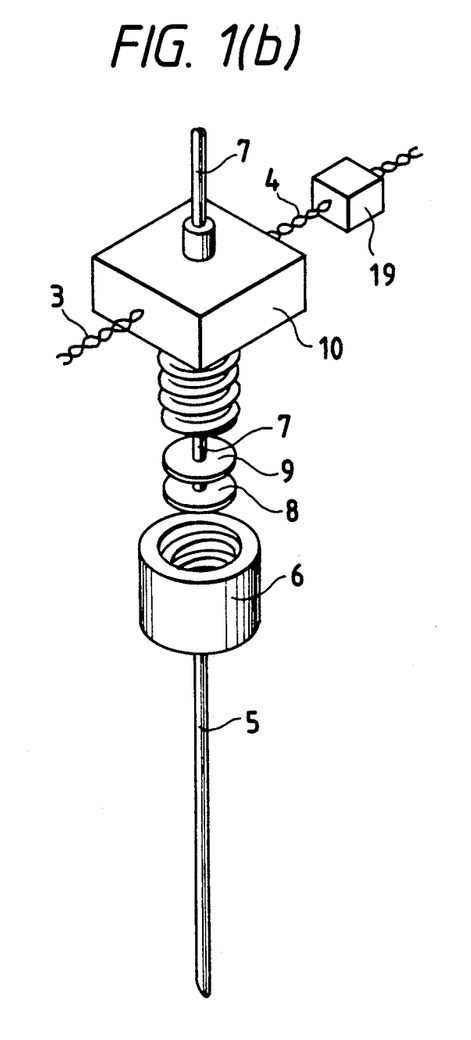
FIGS. 1b and 2b are exploded perspective views of the embodiments shown in FIGS. 1a and 2a, respectively.

FIG 1(a) is a vertical cross section and FIG. 1b is an exploded perspective view showing the sequence of assembly of one embodiment with an air portion detector of a light transmission type. Reference numeral 1 represents a light illuminating member, 2 a light receiving member, 3 and 4 connecting members with light elements, 5 a needle, 6 a needle fixing member, 7 a tube, 8 an expanded portion of the tube 7, 9 a packing, 10 a block, and 19 a comparator. These constitute the air portion detector. The tube 7 is made of transparent or semi-transparent plastic (such as polytetra-fluoro-ethylene). Light from the light illuminating member 1 is radiated into the fluid passage inside the tube 7 and the light that has passed through the fluid in the tube 7 is received by the light receiving member 2.

The amount of light transmitted varies depending on whether the fluid being checked is liquid or gas and constitutes information to be conveyed to the light receiving member 2. Whether the specimen in the passage is gas or liquid can be determined as follows. The outputs of the light receiving member 2 for both the gas and liquid are measured, the comparator is connected after the light receiving member 2 is set to an intermediate value of the two outputs, and the signal from the light receiving member 2 is compared with the comparator's set value.

The needle fixing member 6 that rigidly supports the needle 5 is connected to and screwed over the block 10 with the packing 9 interposed therebetween. The block 10 is provided with a passage which is continuous with and almost equal in diameter to the narrow specimen passage in the needle 5. The light illuminating member 1 and the light receiving member 2 are arranged so as to closely face each other with the passage in the block passing perpendicularly therebetween. In this arrangement an air portion such as fine air bubbles pass immediately before the light receiving member 2 and thus can reliably be detected. The detected fine air bubble, though not shown can be removed from the tip of the needle 5 by discarding only a small amount of air-laden specimen, thus wasting a minimal amount of specimen.

The air-mixed specimen may either be removed from the needle end or by a change-over valve installed in the tube 7 following the needle 5. In either case, when the air bubbles are drawn in from the needle end and detected, they can be removed by discharging the minimal amount of air-mixed specimen at an appropriate timing.

Figure 2A:
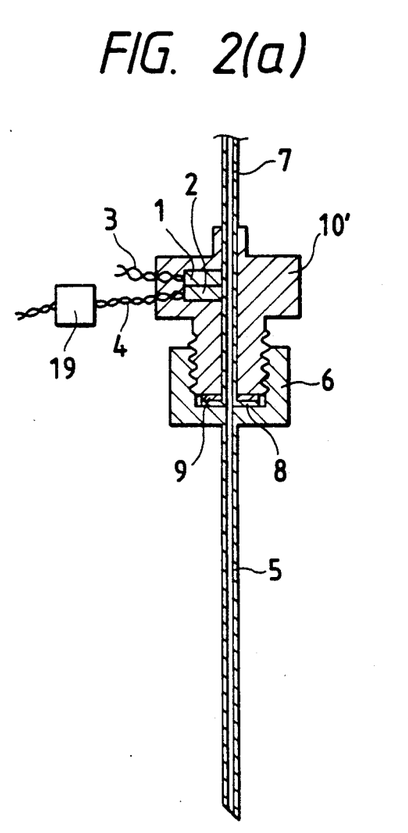
Figure 2B:
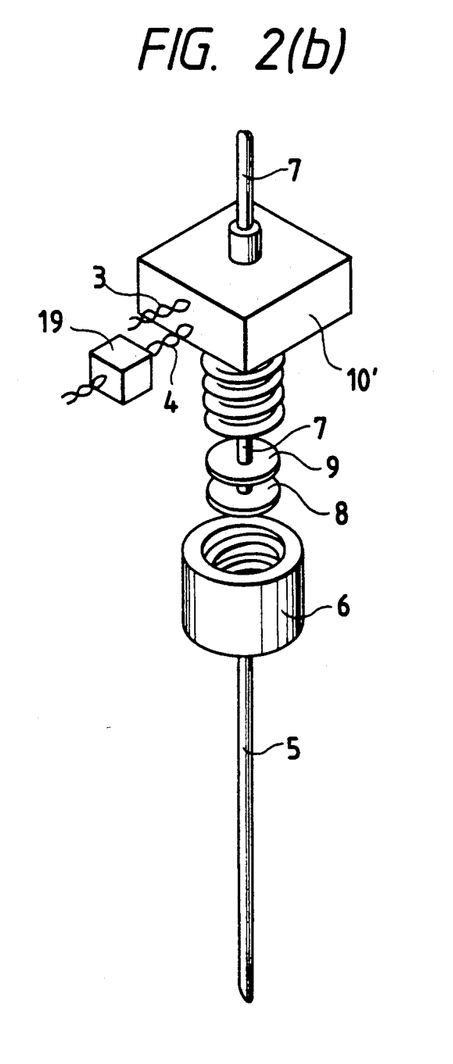

FIG. 2(a) is a vertical cross section and FIG. 2(b) is an exploded perspective view showing the sequence of assembly of another embodiment with an air portion detector of the light reflecting type. Parts identical with those in FIGS. 1(a) and (b) are given like reference numbers and their descriptions are omitted. In the figures, 10' designates a block. The output of the light receiving member 2 varies depending on whether the fluid is gas or liquid. As explained earlier referring to FIG. 1(a), the comparator 19 is installed after the light receiving member 2 to reliably detect an air portion such as fine air bubbles. In the FIG. 2(a) embodiment also, the block 10' has a fluid passage which is continuous with the narrow specimen passage in the needle and which is almost equal in diameter to the needle passage. Like the embodiment of FIG. 1(a), the light illuminating member 1 and the light receiving member 2 are arranged so as to closely face each other with the passage in the block passing perpendicularly therebetween.

Figure 3A:
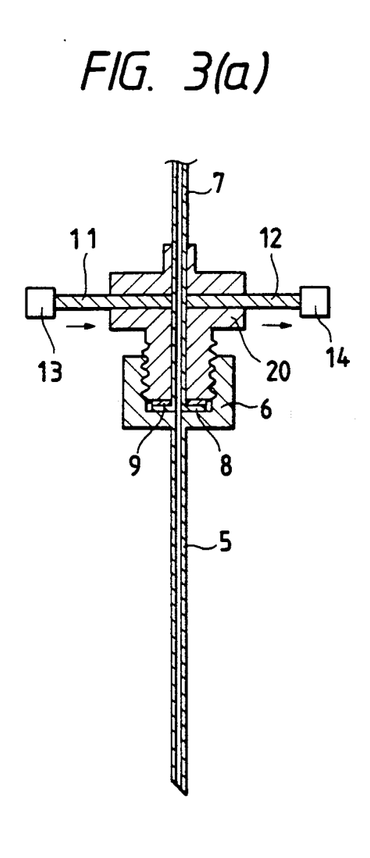
FIGS. 3a, 3b, 3c, 4a and 4b are vertical cross-sectional views of embodiments of this invention in which optical fibers are connected to the light source and light receiving member.
Figure 3B:
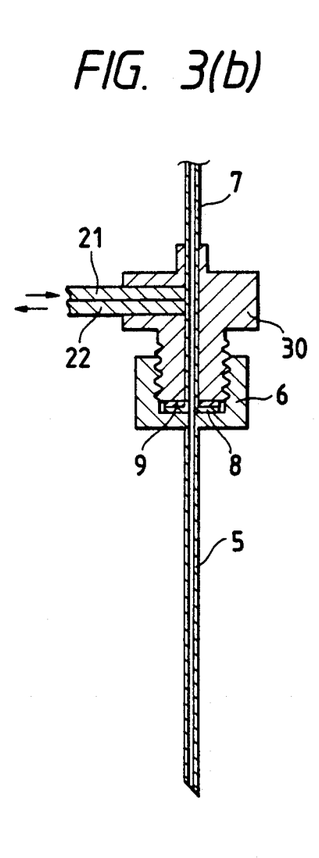
Figure 3C:
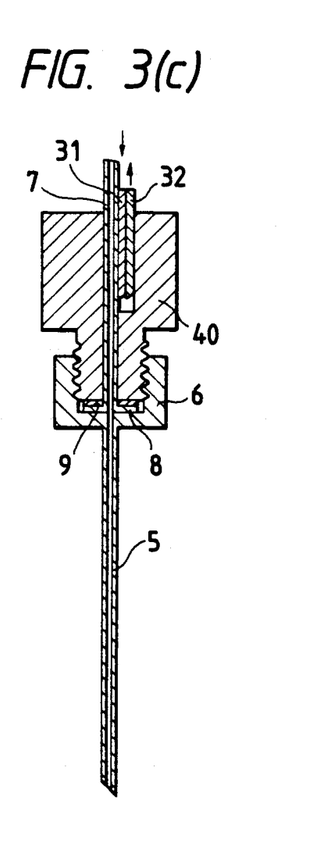

FIGS. 3(a)-(c) are vertical cross sections of autosamplers using an optical fiber in the specimen check section. FIG. 3(a) represents a light transmission type, and FIG. 3(b) and 3(c) represent a light reflection type. These types using optical fibers have the advantage of a simple construction and are practical where the specimen is drawn in through direct contact with cleaning liquid. The air portion detector in the three optical fiber embodiments consists of a light illuminating optical fiber 11, 21, 31, a light receiving optical fiber 12, 22, 32, a light source 13 (not shown in FIG. 3(b) and 3(c)), a light receiving element 14 (not shown in FIG. 3(b) and 3(c)), a needle 5, a needle fixing member 6, a tube 7, an expanded portion 8 of the tube 7, a packing 9, and a block 20, 30, 40. The light illuminating optical fiber 11, 21, 31 is connected at its end with a light source 13 such as light emitting diode, as shown in FIG. 3(a). The light receiving optical fiber 12, 22, 32 is connected at its end with a light receiving element 14 such as phototransistor connected to the comparator, as shown in FIG. 3(a). In FIGS. 3(a) and 3(b), the optical fiber is cut and the cut end surfaces are polished. In FIG. 3(c), the optical fiber end is cut at 45 degrees and the cut end surfaces are coated with light reflecting metal so that the light is reflected at 90 degrees. Any of these three types—FIGS. 3(a), 3(b) and 3(c)—can be chosen according to the construction of the specimen suction member and its associated parts.

In these embodiments, the block 20, 30, 40 is provided with a fluid passage which is continuous with and equal in diameter to the narrow specimen passage in the needle, as in the first embodiment of FIG. 1(a).

Figure 4A:
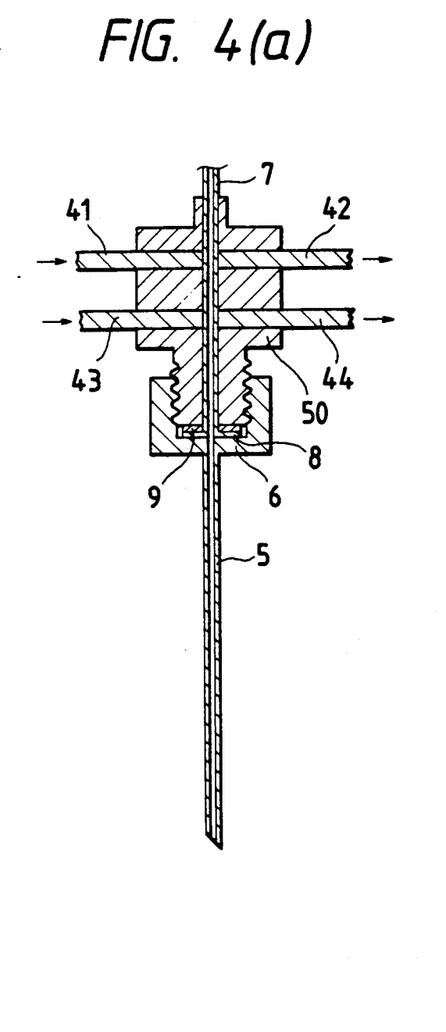
Figure 4B:
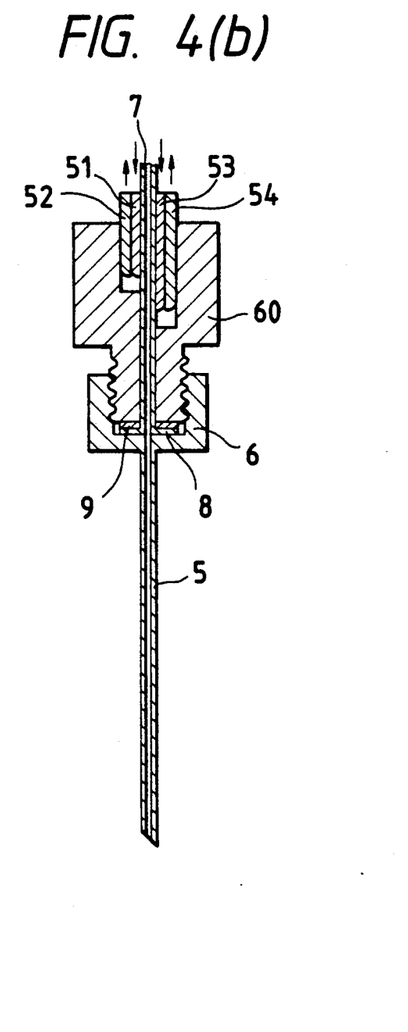

FIGS. 4(a) and 4(b) are vertical cross sections of further embodiments having the air portion detector using optical fibers, in which two optical fibers are provided a specified distance apart. FIG. 4(a) represents a light transmission type and FIG. 4(b) represents a light reflection type. In this embodiment, an air layer for preventing specimen diffusion is inserted between the cleaning liquid and the specimen. This construction is useful when it is desired to distinguish specimens from the undesired air portion in the specimens and to introduce only the specimens into the apparatus. The air portion detector comprises a light illuminating optical fiber 41, 43, 51, 53, a light receiving optical fiber 42, 44, 52, 54, a needle 5, a needle fixing member 6, a tube 7, an expanded portion 8 of the tube 7, a packing 9, and block 50, 60. The light elements (not shown) connected to the ends of the light illuminating and light receiving optical fibers are identical with those used in the embodiment of FIG. 3(a). The feature of this embodiment is that the two sets of light receiving element members are spaced a specified distance from each other and that an AND circuit is provided after the two comparators. The AND circuit decides that undesired air portions have been drawn in only when two light receiving elements detect the gas phase simultaneously. The deliberately inserted air layer for preventing diffusion of the specimen is usually short, but long enough to separate the cleaning liquid and the specimen. When the light receiving element members detect an air layer which is shorter than the specified distance, it decides that the air layer detected is not an unwanted air portion in the specimen and will operate normally. While it is possible to detect an air portion of very small size stated above, it is also possible to detect an air layer longer than the specified length by the same detecting mechanism. To identify the long air layer, the discharging operation must be kept inactivated until the final decision is made, i.e., until the air layer has moved the specified distance.

In this way, the air layer deliberately inserted between the cleaning liquid and the specimen to prevent diffusion of the specimen can be identified by the two light receiving element members and the AND output. In terms of cost, however, the following method is more practical. That is, the air lump detector in FIGS. 4(a) and 4(b) may be provided with only one light sensing member, as in the case of FIGS. 1(a) through 3(c). When the information from one light illuminating member representing the air portion persists for more than a specified period of time, it is decided that a gas lump or bubble other than the specimen diffusion prevention air layer has been taken into the apparatus. For example, in FIGS. 4(a) and 4(b), let us consider the case where the light illuminating optical fiber 41, 51 and the light receiving optical fiber 42, 52 are removed. Immediately before the specimen is drawn in through the needle 5, the fluid passage is filled with cleaning liquid except at the tip of the needle 5, with an air layer formed at the needle tip. As the specimen is introduced into the needle 5, the air layer disposed between the cleaning liquid and the specimen takes a certain time to pass the light detecting member—the light illuminating optical fiber 43 and the light receiving optical fiber 44 in FIG. 4(a) and, in FIG. 4(b), the light illuminating optical fiber 53 and the light receiving optical fiber 54. The time required for the air layer to pass the light detecting member is determined from the length of the air layer and the velocity of specimen being introduced, and it is possible to set the passing time with a sufficient margin. With the air portion detector given the above setting, when air is drawn in instead of liquid specimen or when specimen mixed with air portion such as the air bubbles is introduced, the time it takes for the air to pass the light detecting member is longer than the setting time. If the air portion detected is shorter than the specified time duration, then the air portion detector decides that the air portion is the air layer for preventing the specimen diffusion. In this way, the deliberately inserted specimen separation air layer is distinguished from air portion in the liquid specimen. An integrating circuit is provided at the output of the light receiving element (not shown) attached to the end of the light receiving optical fiber 44, 54. The output of the integrating circuit is then fed, either directly or through a hold circuit, to the comparator which has a specified setting. This method allows elimination of one set of optical fibers and light emitting and light receiving elements, and it only needs addition of a simple circuit. This simplifies the structure of the air portion detector.

Figure 11A:
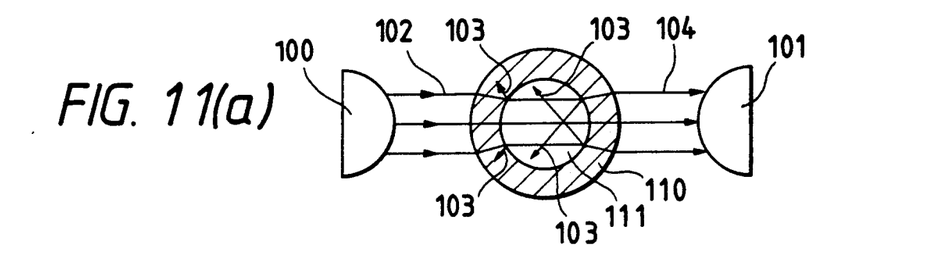
FIGS. 11(a), 11(b), 12(a) and 12(b) are schematic diagrams showing the working principle of this invention.
Figure 11B:
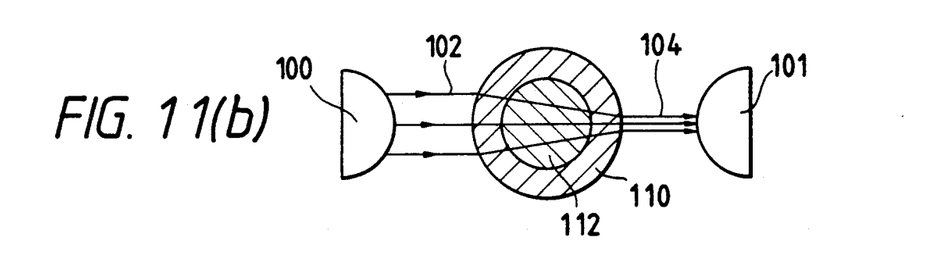
Figure 12A:
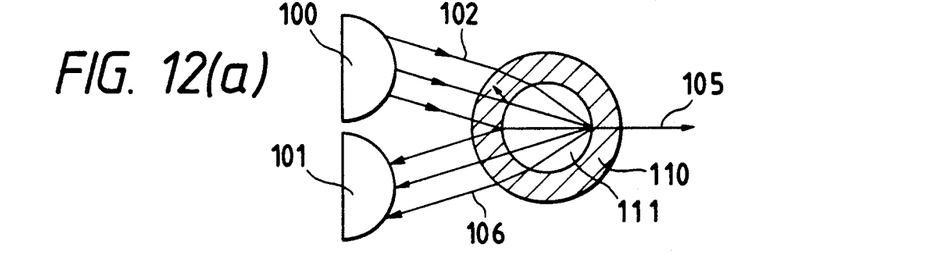
Figure 12B:
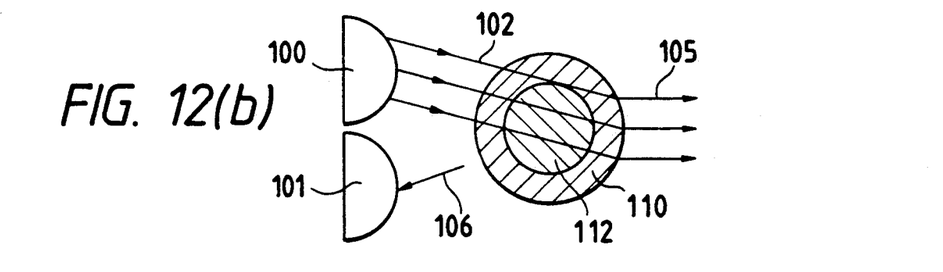

In the above embodiments, we have explained two methods of checking the specimen drawn into the needle by using light, i.e., one using the transmitted light that has passed through the fluid passage through which the specimen is flowing, and one using the light reflected from the fluid passage. The principle of the transmitted light method is shown in FIGS. 11(a) and 11(b) in cross section, and the principle of the reflected light method is shown in FIGS. 12(a) and 12(b) in cross section. FIGS. 11(a) and 12(a) represent the case where gas is flowing in the passage. FIGS. 11(b) and 12(b) represent the case where liquid is flowing in the passage. Reference number 100 denotes the light illuminating member, 101 a light receiving member, 102 an incident light, 103 and 106 reflected light, 104 and 105 transmitted light, 110 a transparent or semitransparent tube, 111 gas, and 112 liquid. The tube 110 and the liquid 112 have almost the same refractive indexes, greater than that of the gas 111.

In the case of FIG. 11(a) where the gas 111 is present in the passage, the light is reflected by the boundary between the tube 110 and the gas 111. In the case of FIG. 11(b) where the liquid 112 is present in the passage, no light is reflected and the liquid 112 works as a lens. As a result, the light transmission factor is greater for the liquid 112 in the passage. The signal for making a final decision is taken from the comparator whose setting is set at an intermediate value between the output of the light receiving member 101 when the fluid in the passage is gas 111 and the output when it is liquid 112.

In the light reflection method of FIGS. 12(a) and 12(b), as mentioned earlier, reflection from the boundary between the gas 111 and the tube 110 is greater than from the boundary between the liquid 112 and the tube 110. Therefore, the output of the light receiving member 101 for the gas 111 is higher than for the liquid 112, which is reverse to the case of the light transmission method. In FIGS. 11 and 12, the refractive indexes of the liquid 112 and tube 110 are slightly different, depending on the materials, so that the actual working state is not as ideal as mentioned above. Furthermore, reflection also occurs at the boundary between the outer wall of the tube 110 and the outer air. The explanation of this phenomenon is not given as it is similar to that of FIGS. 11(a), (b) and FIG. 12(a), (b).

Figure 5:
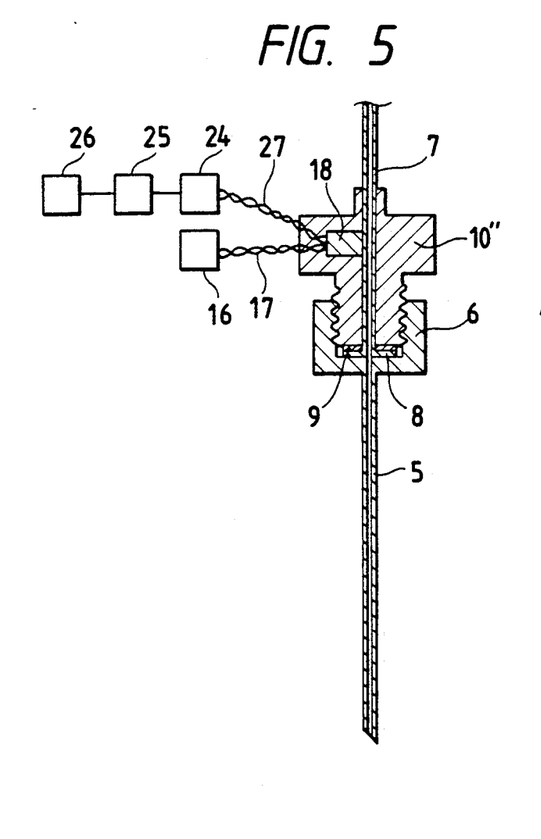
FIG. 5 is a vertical cross-sectional view of one embodiment of this invention using ultrasonic waves.

FIG. 5 is a vertical cross section of a further embodiment of this invention that uses an ultrasonic system for the specimen detector. The detector of FIG. 5 consists of a needle 5, a needle fixing member 6, a tube 7, an expanded portion 8 of the tube 7, a packing 9, a block 10", a piezoelectric element 18 for sending and receiving ultrasonic waves, a drive circuit 16 for the piezoelectric element 18, a detecting circuit 24 for the piezoelectric element 18, a converter circuit 25, a comparator 26, and lead wires 17, 27. The ultrasonic wave is sent out from the piezoelectric element 18 and reflected from the boundary between the fluid and the tube 7. There is a difference in intensity between the reflected ultrasonic waves when the fluid drawn into the needle 5 is gas and when it is liquid. This difference is caused by the differing acoustic impedances for ultrasonic waves at the tube-liquid boundary and at the tube-gas boundary. In other words, the reflected ultrasonic wave from the gas is higher in intensity than from the liquid. The reflected ultrasonic waves are detected by the detecting circuit 24 and the detected peak values of the reflected waves are converted by the converter circuit 25 into d.c. voltages, which are proportional to the magnitudes of the peak values. The converted d.c. voltages are entered into the comparator 26, which is installed after the converter circuit 25. The comparator 26 is set at an intermediate value between the converter circuit outputs for the gas and the liquid. From a signal produced by the comparator 26, it is possible to determine whether the fluid in the passage is gas or liquid.

Figure 6:
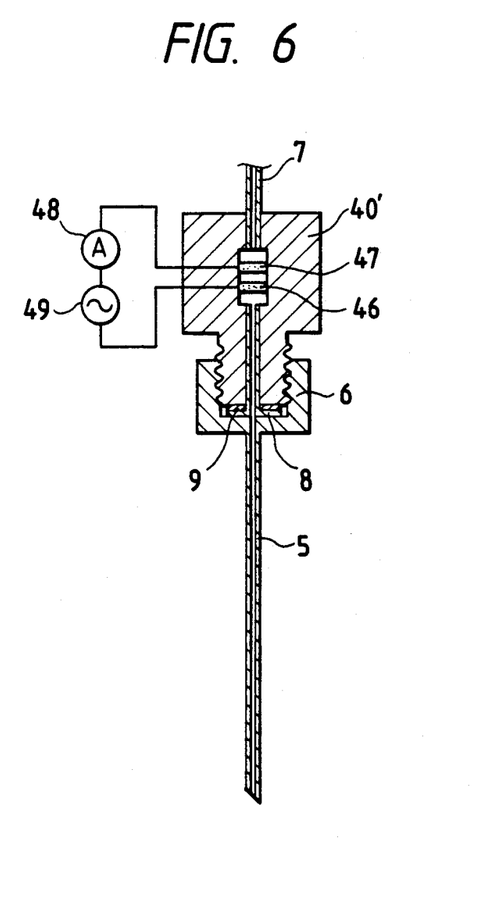
FIG. 6 is a vertical cross-sectional view of one embodiment of this invention in which electrodes are embedded in a block to detect air portion electrochemically.

FIG. 6 is a schematic vertical cross section of a further embodiment of this invention using an electrochemical detecting method. The detector of FIG. 6 consists of a needle 5, a needle fixing member 6, a tube 7, an expanded portion 8 of the tube 7, a packing 9, a block 40', electrodes 46, 47, an ammeter 48, and an a.c. power source 49. The electrodes 46, 47 may be formed of a glassy carbon net electrode or fiber bundle electrode. The a.c. power source is connected between the two electrodes 46, 47 to generate a.c. voltage. While the power source may be a d.c. source, the a.c. power source 49 is used here to remove the influence of polarization. A current flowing between the electrodes 46, 47 is measured by the ammeter 48 to detect electric resistance or electric conductivity. When liquid is drawn into the needle 5, current is conducted by ions in the liquid. On the other hand, when gas is drawn, almost no current flows. So, the gas and the liquid can be distinguished. In this embodiment also, the comparator is installed behind the ammeter 48. Although in the figure the passage containing the electrodes 46, 47 is shown significantly wide, it must be formed almost equal in inner diameter to the needle 5 in order to enable detection of very fine air bubbles.

Figure 7:
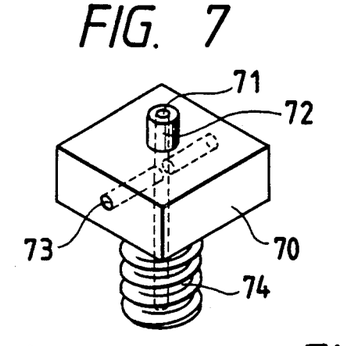
FIG. 7 is a perspective view of one embodiment of the block used in this invention.

FIG. 7 is a perspective view of one embodiment of the block used in the specimen detector of this invention. The block 70 consists of a tubal through-hole 71, a tube protector 72, an optical fiber insertion hole 73, and a connector 74 for the needle fixing member. The block is manufactured by first cutting a lump of opaque material to form a block member with the tube protector 72 and the connector 74 and then drilling the tubal through-hole 71 and the optical fiber insertion hole 73 therein.

Figure 8A:
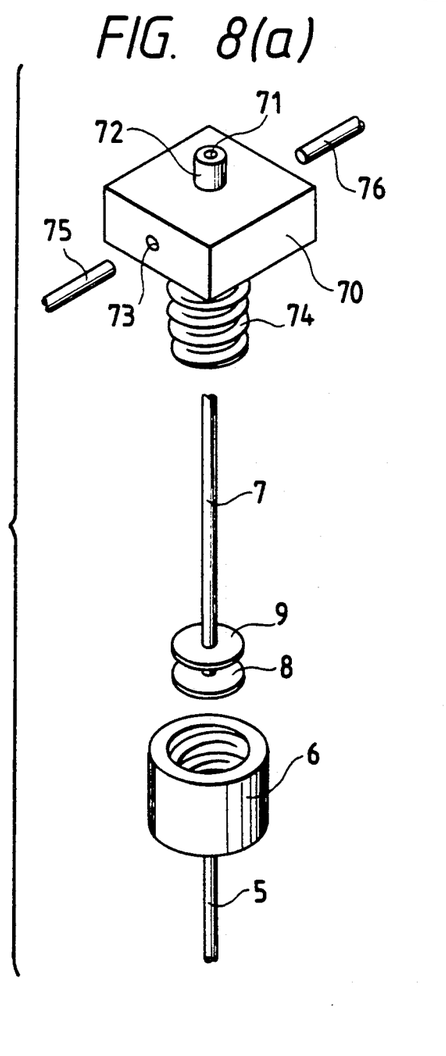
FIGS. 8(a) and 8(b) are perspective views of one example of a method of manufacturing the apparatus of this invention.
Figure 8B:
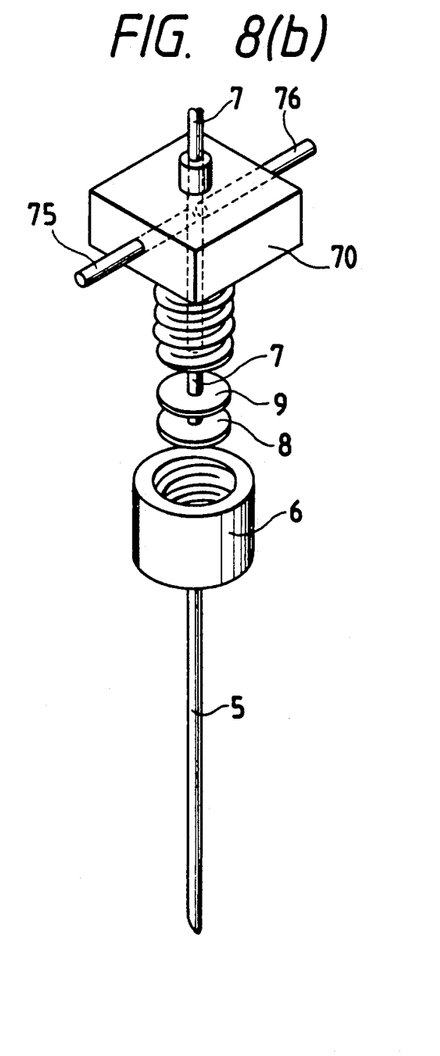

FIGS. 8(a) and 8(b) are perspective views showing the process of manufacturing the specimen detector of this invention.

FIG. 8(a) is a perspective view immediately after the assembling has been started and FIG. 8(b) is a perspective view immediately before completion. As shown in FIGS. 8(a) and 8(b), the constitutional elements include a needle 5, a needle fixing member 6, a tube 7, an expanded portion 8 of the tube 7, a packing 9, a tubal through-hole 71, a tube protector 72, an optical fiber insertion hole 73, a connector 74, a block 70, a light illuminating optical fiber 75, and a light receiving optical fiber 76.

Figure 9:
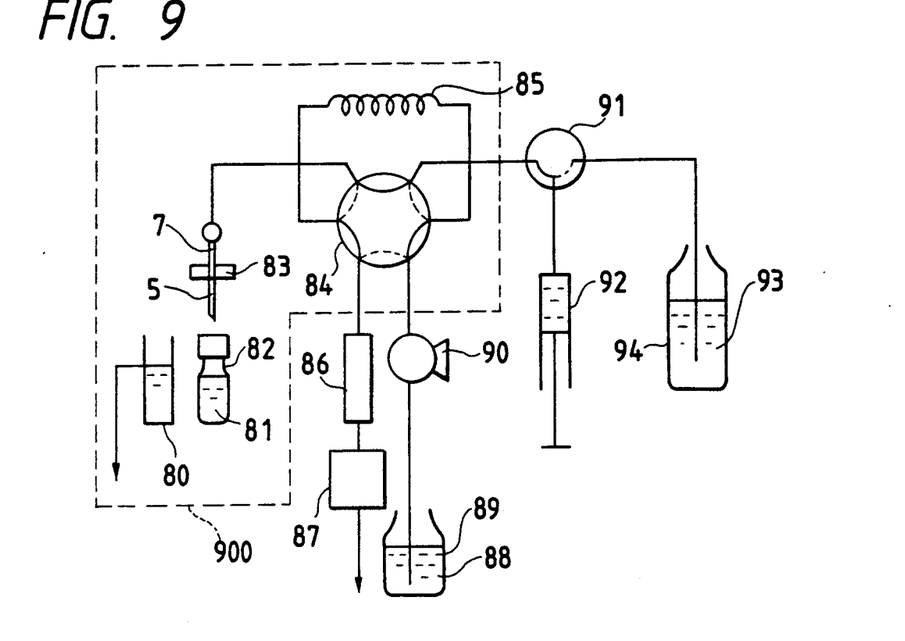
FIGS. 9 and 10 are schematic diagrams of example liquid chromatographs to which an autosampler equipped with the apparatus of this invention is applied.

FIG. 9 is a schematic diagram of a liquid chromatograph, an example of application of the autosampler (enclosed by broken line 900) of this invention using the detector shown in FIGS. 1 through 8. The liquid chromatograph consists of a cleaning port 80, a specimen 81, a specimen bottle 82, a specimen detector 83, a needle 5, a tube 7, a 6-way valve 84, a specimen loop 85, an eluent 88, an eluent container 89, a pump 90 a separation column 86, a detector 87, a 3-way cock 91, a syringe 92, a cleaning liquid 93, and a cleaning liquid container 94. In this autosampler, the specimen 81 is introduced into the liquid chromatograph as follows. First, the 3-way cock 91 is set as shown by the broken line and the syringe 92 is pulled to draw the cleaning liquid 93 into it. Next, the 3-way cock 91 is switched as shown by the solid line and the 6-way valve 84 is also switched as shown by the solid line. The needle 5 is moved immediately above the cleaning port 80 and the syringe 92 is pushed to cause the cleaning liquid in the syringe 92 to flow through the passage to clean it. At this time the pump 90 is delivering the eluent 88, and the passage through the specimen loop 85, separation column 86, and detector 87 is in the initial condition. Then, the 6-way valve 84 is switched as shown by the broken line and the needle 5 is inserted into the specimen bottle 82. The syringe 92 is pulled to introduce the specimen 81 into the specimen loop 85. The tube 7 is mounted with a specimen detector 83 of this invention, which prevents the 6-way valve 84 from being switched to the solid line passage when air bubbles, not the specimen 81, are drawn in. When the specimen 81 fills the specimen loop 85, the 6-way valve 84 is switched to the solid line passage for performing analysis.

Figure 10:
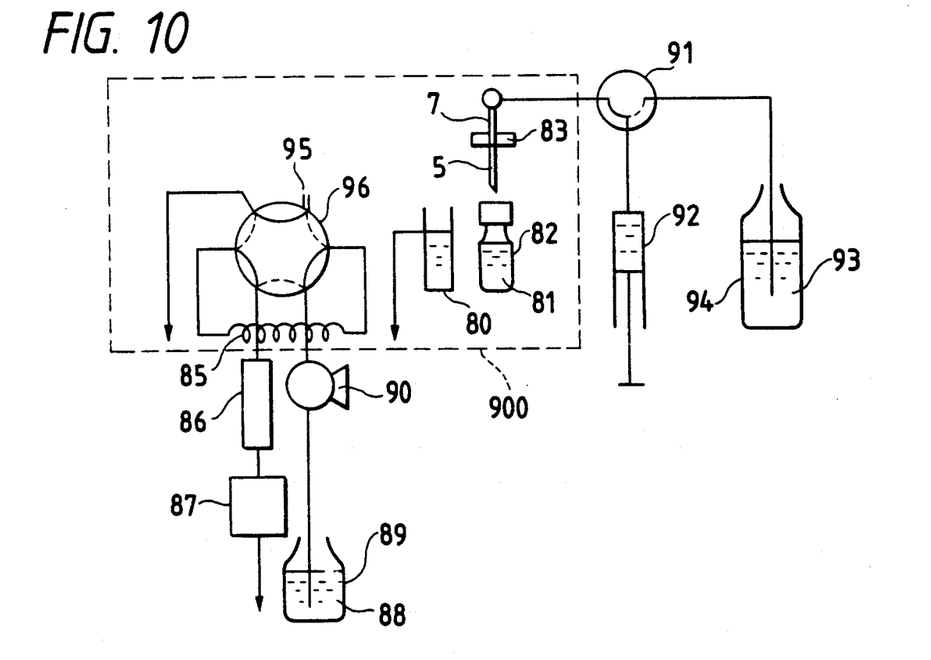

FIG. 10 is a schematic diagram of another liquid chromatograph that applies the autosampler 900 of this invention using the detector shown in FIGS. 1(a) through 8(b). The component that are identical with those of FIG. 9 are given like reference numerals and their explanations are omitted. In FIG. 10, the 6-way valve 96, which takes the place of valve 84 of FIG. 9, is connected with an injection port 95 so that the 6-way valve 69 can be bypassed in cleaning the needle 5. According to this autosampler, the specimen 81 is introduced into the liquid chromatograph in the following sequence. First, the 3-way cock 91 is set to the position shown by the broken line and the cleaning liquid 93 is drawn in by the syringe 92. Then, the 3-way cock 91 is switched to complete the passage indicated by the solid line, and the 6-way valve 96 is switched to the solid line passage. The needle 5 is moved to the injection port 95 and the syringe 92 is pushed to clean the passage. At this time, the pump 90 is delivering eluent 88 and therefore the passage in the specimen loop 85, separation column 86 and the detector 87 is in the initial state. Next, the 6-way valve 96 is switched to the broken line passage; the needle 5 is inserted into the specimen bottle 82; and the syringe 92 is pulled to draw the specimen into the passage. After this, the needle 5 is moved to the injection port 95 to introduce the specimen into the specimen loop 85. As in FIG. 9, when an air layer for preventing specimen diffusion is to be inserted between the cleaning liquid 93 and the specimen 81 in the embodiment of FIG. 10, it would be effective to use two sensing members as illustrated in FIG. 4.

As explained above, in the autosampler according to this invention, since even a small amount of air is reliably distinguished from normal specimens when a specimen mixed with air bubbles is introduced from the specimen bottle or when air is drawn in from an empty specimen bottle, the reliability of the specimen analyzing system using the autosampler can be significantly improved.

We claim:

1. An autosampler with apparatus for detecting an air bubble in a liquid specimen, comprising:
   a container for containing the specimen;
   a needle for drawing the specimen from the container into a passage in the needle;
   a needle fixing member supporting the needle;
   a block upon which the needle fixing member is detachably connected, the block having a passage therein having a cross section almost equal to the cross section of the needle passage;
   a suction means for drawing in the specimen by suction through the passages in the needle and the block;
   a discharge means for discarding a specimen containing an air bubble drawn in by the suction mechanism; and
   a detecting means arranged in the block to face the passage in the block for detecting an air bubble in the specimen based on optical changes in the specimen flowing through the passage in the block;
   whereby the discharge means is activated by the detecting means.

2. An autosampler with apparatus for detecting an air bubble in a liquid specimen according to claim 1, wherein the detecting means detects an amount of attenuation in intensity of light radiated from a light illuminating member of the detecting means provided near the passage in the block, wherein the light passes through the specimen in the passage in the block and is received by a light receiving member of the detecting means in the block.

3. An autosampler with apparatus for detecting an air bubble in a liquid specimen according to claim 2, wherein the light illuminating member is an optical fiber for introducing light from a light source into the specimen in the passage in the block, and the light receiving member is an optical fiber for transferring the light that has passed through the specimen.

4. An autosampler with apparatus for detecting an air bubble in a specimen according to claim 1, wherein the detecting means detects changes in intensity of light radiated from a light illuminating member provided near the passage in the block, wherein the light is received by a light receiving member in the block.

5. An autosampler with apparatus for detecting an air bubble in a liquid specimen according to claim 4, wherein the light illuminating member is an optical fiber for introducing light from a light source into the specimen in the passage in the block, and the light receiving member is an optical fiber for transferring the light that has been reflected by the specimen.

6. A autosampler with apparatus for detecting an air bubble in a liquid specimen according to claim 1, wherein the detecting means comprises an ultrasonic wave transducer provided near the passage in the block to detect change in acoustic impedance of the specimen in the passage in the block.

7. An autosampler with apparatus for detecting an air bubble in a liquid specimen according to claim 1, wherein the detecting means includes two electrodes inserted into the passage in the block to detect change in electric property between the electrodes.

8. An autosampler with apparatus for detecting an air bubble in a liquid specimen according to claim 1, wherein the detecting means produces an output only when the property change of the specimen passing through the passage in the block exceeds a specified duration of time.

* * * * *